United States Patent [19]

Takada et al.

[11] Patent Number: 5,760,244
[45] Date of Patent: Jun. 2, 1998

[54] PROCESS FOR THE PREPARATION OF 3-ISOXAZOLECARBOXYLIC ACID

[75] Inventors: Susumu Takada, Kawanishi; Nobuo Chomei, Sakai; Masaaki Uenaka, Osaka, all of Japan

[73] Assignee: Shionogi & Co., Ltd., Osaka, Japan

[21] Appl. No.: 901,133

[22] Filed: Jul. 28, 1997

Related U.S. Application Data

[62] Division of Ser. No. 687,330, Aug. 7, 1996, Pat. No. 5,696,271.

[30] Foreign Application Priority Data

Feb. 16, 1994 [JP] Japan ................... 6-19380

[51] Int. Cl.⁶ .................................. C07D 261/08
[52] U.S. Cl. .................................. 548/248
[58] Field of Search .................................. 548/248

[56] References Cited

U.S. PATENT DOCUMENTS

| | | | |
|---|---|---|---|
| 5,374,605 | 12/1994 | Hellenbach et al. | 504/252 |
| 5,399,577 | 3/1995 | Shindo et al. | 514/378 |
| 5,514,505 | 5/1996 | Limburg et al. | 430/41 |
| 5,633,272 | 5/1997 | Talley et al. | 514/378 |

OTHER PUBLICATIONS

"Dehydrochlorination of Hydroximic Acid Chlorides by the Use of Organotic Compounds: An Application for Synthesis of Isoxazolines and Isoxazoles", Moriya et al., J. Chem. Soc. pp. 17–18 vol. 1., 1991.

O. Mumm et al., "Uber die freie Aceton–oxaisaure und ihre Abkommlinge", Chemische Berichte, vol. 45, 1912, pp. 3042, 3045, 3046.

*Primary Examiner*—Joseph McKane
*Attorney, Agent, or Firm*—Foley & Lardner

[57] ABSTRACT

A process for the preparation of 3-isoxazolecarboxlic acid which is an intermediate for prepearing useful compounds is provided, said process being characterized in that a compound of formula (I) is reacted with hydroxylamine to obtain a compound of formula (II), and the compound thus obtained is treated with an alkali:

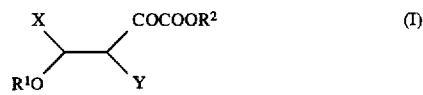

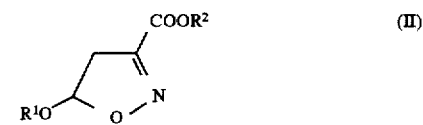

wherein $R^1$ is a lower alkyl, $R^2$ is a carboxy protecting group, X is a halogen atom, and Y is a hydrogen atom, or X and Y together may form a single bond.

1 Claim, No Drawings

PROCESS FOR THE PREPARATION OF 3-ISOXAZOLECARBOXYLIC ACID

This application is a division of application Ser. No. 08/687,330, filed Aug. 7, 1996 now U.S. Pat. No. 5,696,271 which is the national stage of PCT/JP95/00211 filed Feb. 15, 1995.

FIELD OF THE INVENTION

This invention relates to a process for the preparation of 3-isoxazolecarboxylic acid which is useful as an intermediate for producing condensed imidazopyridine derivatives which are described, for example, in Japanese Patent Publication (Kokai) No. 286973/1993 and its corresponding European Patent Publication No. 556008A.

DESCRIPTION OF PRIOR ART AND PROBLEMS TO BE SOLVED

3-Isoxazolecarboxylic acid has been synthesized by various methods. For instance, as shown in the reaction scheme below, ethoxycarbonylnitrile oxide was reacted with vinylethyl ether to obtain ethyl 5-ethoxyisoxazoline-3-carboxylate, and then the ethoxy group was removed to produce ethyl 3-isoxazolecarboxylate [Raymond Paul and Serge Tchelitcheff, Bull. Soc. Chim. France 1962, 2215].

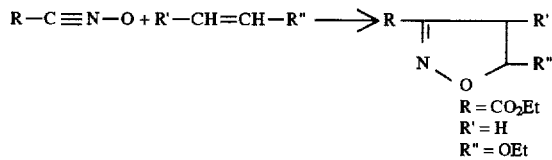

This method, however, has a disadvantage that the ethyl chloroximinoactate, a starting material of the nitrile oxide, upon touching skin, could cause a rash on the skin.

Further, in J. Chem. Soc., Chem. Commun., 17 (1991), a method for the preparation of ethyl 3-isoxazolecarboxylate is described. This method uses ethyl chloroximinoacetate as a starting material, which also causes a rash on the skin, and it is hard to handle.

J. Org. Chem. 26, 2976 (1961) discloses, a method for the preparation of 3-isoxazolecarboxylic acid as shown in the reaction scheme below. This method is not suitable for industrial production of the acid because of its poor reaction efficiency.

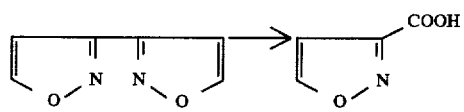

In view of the above problems, the inventors of the present invention have explored an industrially-applicable synthetic method for 3-isoxazolecarboxylic acid, and they have developed a novel process for the preparation of the acid.

DETAILED DESCRIPTION OF THE INVENTION

The present invention relates to a process for the preparation of 3-isoxazolecarboxylic acid of the formula (III):

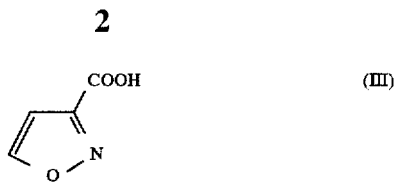

characterized in that a compound of the formula (I):

wherein $R^1$ is a lower alkyl, $R^2$ is a carboxy protecting group, X is a halogen atom, and Y is a hydrogen atom, or X and Y together may form a single bond, is reacted with hydroxylamine to obtain a compound of the formula (II):

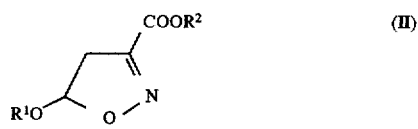

wherein $R^1$ and $R^2$ are as defined above, and then the resultant product is treated with alkali.

Each step of the above overall process also constitues another invention. That is, the process for the production of 5-alkoxyisoxazoline-3-carboxylic acid derivatives of the above formula (II), which process is characterized in that a compound of the formula (I):

wherein $R^1$, $R^2$, X and Y are as defined above, is reacted with hydroxylamine, is also part of the present invention.

Further, a process for the production of 3-isoxazolecarboxylic acid of the formula (III):

which process is characterized in that a compound of the formula (II):

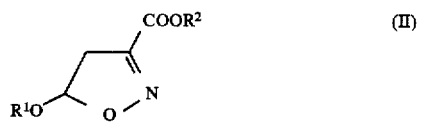

wherein $R^1$ is a lower alkyl and $R^2$ is a carboxy protecting group, is treated with alkali, is also part of the present invention.

The process of the present invention may be shown in the following reaction scheme.

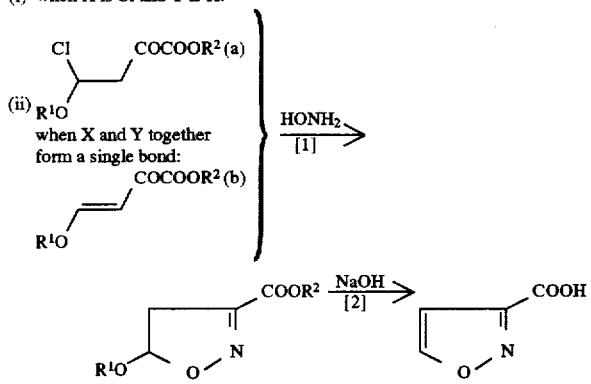

In step[1], the compound (a) or (b) of the formula (I) is reacted with hydroxylamine. The reaction temperature is usually from about −20° to about 80° C., preferably from 0° to 40° C. The reaction is carried out in the presence or absence of a solvent. As the solvent, ethers (ethyl ether, tetrahydrofuran, etc.), aromatic hydrocarbons (benzene, toluene, etc.), and halogenated hydrocarbons (chloroform, dichloromethane, etc.) may be exemplified. Hydroxylamine may be used preferably in an amount of about 1 to 4 molar equivalents to the starting material.

The starting materials (a) and (b) may be prepared according to the following reaction scheme as described in L. F Tietze, Synthesis, 274 (1988):

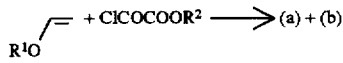

Although this reaction produces a mixture of the compounds (a) and (b), the compound (a) is readily converted into the compound (b) during isolation and purification for example, by distillation, thereby the single compound (b) is obtained. The compound (a) is known to be unstable as intermediate, and it is believed that the compound (a) might be converted into the compound (b) by heating (higher than about 60° C.) or under basic conditions. Incidentally, in the following Example 1, it has been confirmed by NMR analysis that the mixture in which the compound (a) was a main product was produced at the first step.

Therefore, irrespective of the contents of the starting materials (a) and (b) in the mixture, the result would be the same as the case when the compound (a) or (b) is solely used in the reaction. Accordingly, these starting materials (a) and (b) can be used for the reaction without isolation and purification.

The above step[2] is the process in which elimanation of $R^1OH$ and hydrolysis of ester are carried out in a single step.

The reaction is usually carried out in a solvent such as water and alcohols, and preferably at a temperature from about 0° to 50° C. Alkali may be used preferably in an amount of about 1 to 10 molar equivalents to the compound (II).

In general, elimination of an alkoxy group (dealcohol) is usually carried out under acidic condition or heating. It is therefore expected that the elimination of the alkoxy group may be achieved under one of such conditions alone. In the present invention, however, hydrolysis of the ester must be conducted coincidently, and hence the alkali treatment is added.

Theoretically, a carboxy protecting group $R^2$ can be optionally selected from conventional protecting groups as far as it is not deprotected during the reaction (1) but deprotected during the reaction (2). Taking the yield and after-treatment into consideration, however, lower alkyls (in particular, methyl, ethyl, propyl, etc.) or aralkyls (in particular, benzyl, naphthylmethyl, etc.), and the like are preferable.

Examples of the alkali used in the step[2] are hydroxide of alkali metals, alkaline earth metals or ammonium group, and the preferred alkalis are NaOH, KOH, and the like.

The lower alkyls for $R^1$ are straight or branched $C_1$-$C_6$ alkyls such as methyl, ethyl, n-propyl, i-propyl, n-butyl, sec-butyl, t-butyl, n-pentyl, i-pentyl, n-hexyl, and i-hexyl. $C_1$-$C_3$ alkyl is preferred.

The halogens for X are Cl, Br, and the like, and Cl is preferred.

The following examples are provided to illustrate the present invention in more detail, but they are not intended to limit the scope of the present invention.

EXAMPLE 1

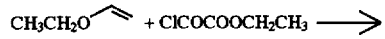

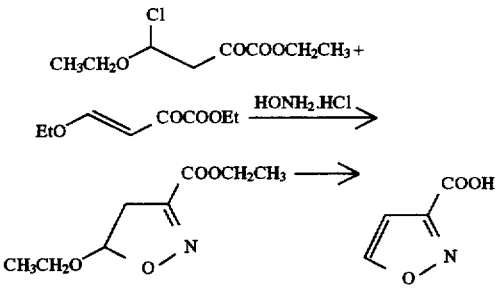

Vinylethyl ether(480 ml) is added to 280 ml of oxalyl chloride at room temperature, and the mixture is stirred for 4 hours to obtain a reaction mixture which contains ethyl 4-ethoxy-4-chloro-2-oxobutylate as a main product.

Ethyl 4-ethoxy-4-chloro-2-oxobutyrate (compound (a))

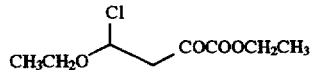

NMR (CDCl$_3$):δ1.24 (3H,t), 1.38 (3H,t), 3.49(1H,m), 3.58(1H,q), 3.65(1H,m), 3.94(1H,q), 4.34(2H,q), 6.01(1H, m) ppm.

The reaction mixture is cooled with ice, and 1680 ml of dry ethanol are added slowly while avoiding occurrence of exothermic reaction, and then 173 g of hydroxylamine hydrochloride is added, and the mixture is stirred at room temperature for 4 hours. The reaction mixture is poured into 3400 ml of water and extracted with ethyl acetate. The extract is washed sequentially with water, an aqueous solution of sodium bicarbonate, and a saturated brine, and dried over anhydrous sodium sulfate. The solvent is distilled off to obtain 468 g of oily residue which contains ethyl 5-ethoxyisoxazoline-3-carboxylate as a main product. To this residue is added 750 ml of 5N sodium hydroxide, and the mixture is stirred at room temperature for 2 hours. To the reaction mixture, 152 ml of concentrated hydrochloric acid is added, and 950 ml of methyl ethyl ketone is added thereto. An additional amount of concentrated hydrochloric acid is added to render the mixture acidic to pH 2. The organic layer is separated, treated with active carbon and anhydrous magnesium sulfate, and evaporated. The resulting residue is crystallized from ethyl acetate, filtered, and recrystallized from ethyl acetate to obtain 97 g of 3-isoxazolecarboxylic acid.

Melting point: 149°–150.5° C. (It is described as 149° C. in R. Cramer and W. R. McCleallan, J. Org. Chem., 26, 2976 (1961))

NMR($d_6$-DMSO): δ6.93(1H,d,J=1.8Hz), 9.14(1H,d,J=1.8Hz), 14.0(1H,br) ppm.

Elementary analysis for $C_4H_3NO_3$:
Calculated (%): C, 42.49; H, 2.67; N, 12.39
Found (%): C, 42.25; H, 2.80; N, 12.12

EXAMPLE 2

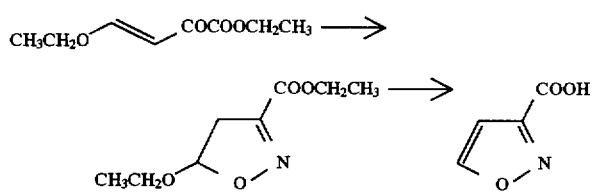

(1) Ethyl 5-ethoxyisoxazoline-3-carboxylate 17.22 g of 4-ethoxy-2-oxo-3-butenoic acid prepared according to the method of L. Tietze et al. (Lutz-F. Tietze, Heinrich Meier and Edgar Voss, Synthesis 1988, 274) are dissolved in 50 ml of anhydrous ethanol, and 7.34 g of hydroxylamine hydrochloride is added thereto, and the mixture is stirred at room temperature for 4 hours. The reaction mixture is added with water and extracted with methylene chloride. The organic layer is washed with water, dried, and evaporated. The resulting residue is distilled under reduced pressure to yield 14.3 g of ethyl 5-ethoxyisoxazoline-3carboxylate. (yield 76%)

Boiling point: 113°–115° C. (2 mmHg)

NMR (CDCl$_3$):δ1.22 (3H,t), 1.38 (3H,t), 3.0–3.4 (2H,m), 3.5–4.0 (2H,m), 4.36 (2H,q), 5.71 (1H,m) ppm.

Elementary analysis for $C_8H_{13}NO_4$:
Calculated (%): C, 51.33; H, 7.00; N, 7.48
Found (%): C, 51.08; H, 7.10; N, 7.25

(2) Isoxazole-3-carboxylic acid 200 ml of 1N sodium hydroxide are added to 24.75 g of ethyl 5-ethoxyisoxazoline-3-carboxylate prepared according to the method of process (1), and the mixture is stirred at room temperature for 2 hours. The reaction mixture is acidified with 26 ml of concentrated hydrochloric acid, and condensed to about ⅓volume under reduced pressure, and cooled. The separated crystalline compound is filtered, washed twice with 30 ml of cold water and dried to yield 13.43 g of the titled compound.

Melting point: 149°–152° C.

What is claimed is:

1. A process for the preparation of 3-isoxazolecarboxylic acid of the formula (III):

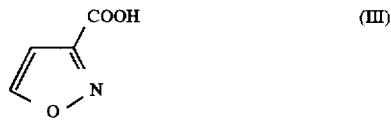 (III)

characterized in that a compound of the formula (II):

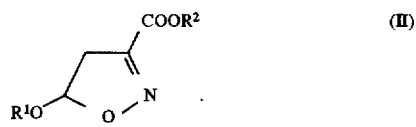 (II)

wherein $R^1$ is a lower alkyl and $R^2$ is a carboxy protecting group, is treated with an alkali.

* * * * *